(12) United States Patent
Yang et al.

(10) Patent No.: US 10,299,678 B2
(45) Date of Patent: May 28, 2019

(54) METHOD AND APPARATUS FOR DETECTING DEHYDRATION

(71) Applicants: Chang Gung Memorial Hospital, Chiayi, Chiayi (TW); National Applied Research Laboratories, Taipei (TW); National Taiwan University, Taipei (TW)

(72) Inventors: Jen-Tsung Yang, Chiayi (TW); Leng-Chieh Lin, Chiayi (TW); I-Neng Lee, Chiayi (TW); Jo-Wen Huang, Chiayi (TW); Jer-Liang Andrew Yeh, Hsinchu (TW); Ming-Yu Lin, Hsinchu (TW); Yen-Pei Lu, Hsinchu (TW); Chih-Ting Lin, Taipei (TW); Chia-Hong Gao, Taipei (TW)

(73) Assignees: CHANG GUNG MEMORIAL HOSPITAL, CHIAYI, Chiayi (TW); NATIONAL APPLIED RESEARCH LABORATORIES, Taipei (TW); NATIONAL TAIWAN UNIVERSITY, Taipei (TW)

( * ) Notice: Subject to any disclaimer, the term of this patent is extended or adjusted under 35 U.S.C. 154(b) by 0 days.

(21) Appl. No.: 15/477,642

(22) Filed: Apr. 3, 2017

(65) Prior Publication Data
US 2017/0290509 A1 Oct. 12, 2017

Related U.S. Application Data

(60) Provisional application No. 62/319,693, filed on Apr. 7, 2016.

(51) Int. Cl.
*A61B 5/00* (2006.01)
*A61B 5/05* (2006.01)
(Continued)

(52) U.S. Cl.
CPC ............ *A61B 5/00* (2013.01); *A61B 5/05* (2013.01); *A61B 5/053* (2013.01); *A61B 5/0537* (2013.01);
(Continued)

(58) Field of Classification Search
CPC .......... A61B 5/00; A61B 5/05; A61B 5/0537; A61B 5/053; A61B 5/14507; A61B 5/4875
See application file for complete search history.

(56) References Cited

U.S. PATENT DOCUMENTS

| 8,702,947 B2 | 4/2014 | Hamada et al. |
| 2002/0127143 A1 | 9/2002 | Kuo |

(Continued)

FOREIGN PATENT DOCUMENTS

| CN | 2052263 U | 2/1990 |
| CN | 101815481 B | 2/2013 |

(Continued)

OTHER PUBLICATIONS

Shirreffs, Susan M. et al., "Urine osmolality and conductivity as indices of hydration status in athletes in the heat." Nov. 1998, Medicine and Science in Sports and Exercise, vol. 30, issue 11, pp. 1598-1602.

(Continued)

*Primary Examiner* — Sean P Dougherty
(74) *Attorney, Agent, or Firm* — Muncy, Geissler, Olds & Lowe, P.C.

(57) ABSTRACT

An apparatus for detecting conductance parameter of high protein body fluid sample is provided. The apparatus includes at least one liquid collection element, and at least two electrodes horizontally aligned in the liquid collection element. Also provided are methods for detecting dehydra- (Continued)

tion in a subject, comprising the steps of measuring the conductance parameter of the saliva of the subject.

7 Claims, 8 Drawing Sheets

(51) Int. Cl.
*A61B 5/053* (2006.01)
*A61B 5/145* (2006.01)
*G01N 33/487* (2006.01)

(52) U.S. Cl.
CPC ........ *A61B 5/14507* (2013.01); *A61B 5/4875* (2013.01); *G01N 33/48707* (2013.01)

(56) References Cited

U.S. PATENT DOCUMENTS

| | | | |
|---|---|---|---|
| 2007/0015287 A1 | 1/2007 | Robbins et al. | |
| 2007/0048224 A1* | 3/2007 | Howell | A61B 5/4277 424/9.1 |
| 2011/0290649 A1* | 12/2011 | Hamada | B03C 5/005 204/547 |
| 2011/0291670 A1* | 12/2011 | Barnard | G01N 27/07 324/601 |
| 2012/0083711 A1 | 4/2012 | Goldstein et al. | |
| 2013/0325356 A1 | 12/2013 | Elashoff et al. | |
| 2015/0216471 A1* | 8/2015 | Goldstein | A61B 10/0051 600/373 |
| 2016/0213316 A1* | 7/2016 | Hyde | A61B 5/4875 |
| 2017/0007172 A1* | 1/2017 | Shaikh-Omar | A61B 5/4277 |

FOREIGN PATENT DOCUMENTS

| | | |
|---|---|---|
| CN | 203447276 U | 2/2014 |
| CN | 102762166 B | 12/2014 |
| CN | 104622514 A | 5/2015 |

OTHER PUBLICATIONS

Fernandes, Luís André et al., "Design and Characterization of an Osmotic Sensor for the Detection of Events Associated With Dehydration and Overhydration." IEEE J. Transl. Eng. Health Med, vol. 1, Aug. 21, 2013, 2700309, 9 pages.

Sezer, Rabia Gonul et al., "Nanoduct Sweat Conductivity Measurements in 2664 Patients: Relationship to Age, Arterial Blood Gas, Serum Electrolyte Profiles and Clinical Diagnosis." J. Clin. Med. Res. Feb. 2013; 5(1): 34-41.

Walsh, Neil P., et al., "Saliva parameters as potential indices of hydration status during acute dehydration." 2004, Medicine and Science in Sports and Exercise, vol. 36, issue 9, pp. 1535-1542.

Walsh, Neil P., et al., "Saliva flow rate, total protein concentration and osmolality as potential markers of whole body hydration status during progressive acute dehydration and rehydration in humans." Archives of Oral Biology (2004) 49, 149-154.

* cited by examiner

METHOD AND APPARATUS FOR DETECTING DEHYDRATION

CROSS-REFERENCE TO RELATED APPLICATION

This application claims priority to U.S. Application No. 62/319,693, filed on Apr. 7, 2016, the entire disclosure of which is incorporated herein by reference.

BACKGROUND OF THE INVENTION

Field of the Invention

The present invention relates to apparatus for measuring conductance parameters in a high protein sample and/or methods for diagnosing dehydration in a subject.

Description of Related Art

Dehydration is a condition that occurs when the loss of body fluid, mostly water, exceeds the amount that is taken in. Fluid losses of between 2-3% of body mass detrimentally affect cardiovascular and renal function, thermal dissipation and exercise performance. More severe dehydration can lead to acute ischemic attack, stroke or even death.

Methods for assessing hydration status include periodically weigh a subject under controlled conditions or testing specific parameters in the urine or blood. For example, urine specific gravity and output are commonly used in clinical setting. Hydration status can also be assessed using a blood sample, as an increase in plasma urea, creatinine or urea over creatinine ratio indicates dehydration. However, blood collection is invasive and can be highly impractical in many situations, especially in children.

There is an unmet need to develop an easy, rapid and non-invasive method to diagnose dehydration. The present invention provide methods and apparatus for diagnosing dehydration to satisfy these and other needs.

SUMMARY OF THE INVENTION

In one embodiment, the present invention provides an apparatus for detecting the conductance parameter of a high protein sample, comprising a liquid collection element and at least two electrodes horizontally aligned. In an exemplary embodiment, the apparatus comprises a first electrode and a second electrode in the liquid collection element, each electrode having a top surface, a bottom surface and at least one edge, wherein the edge of the first electrode is facing said edge of the second electrode with a gap between the edges.

In another embodiment, the present invention provides methods for detecting dehydration in a subject, comprising the step of measuring the conductance parameter of the saliva of the subject, wherein the saliva conductance parameter is electric conductance or impedance, and a higher saliva electric conductance in the subject, relative to the saliva electric conductance of a non-dehydrated subject, is indicative the subject is dehydrated or a lower saliva impedance in the subject, relative to the saliva impedance of a non-dehydrated subject, is indicative the subject is dehydrated.

In yet another embodiment, the present invention provides the use of the apparatus described herein for measuring conductance parameter of a high protein sample for detecting dehydration of a subject.

Also provided are apparatus for measuring the conductance parameter of the saliva in the manufacture of a kit for detecting dehydration in a subject.

Statements containing these terms should be understood not to limit the subject matter described herein or to limit the meaning or scope of the patent claims below. Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification, any or all drawings and each claim.

BRIEF DESCRIPTION OF THE DRAWINGS

The exemplary embodiment(s) of the present invention will be understood more fully from the detailed description given below and from the accompanying drawings of various embodiments of the invention, which, however, should not be taken to limit the invention to the specific embodiments, but are for explanation and understanding only.

DETAILED DESCRIPTION OF THE PREFERRED EMBODIMENTS

Figure 1:
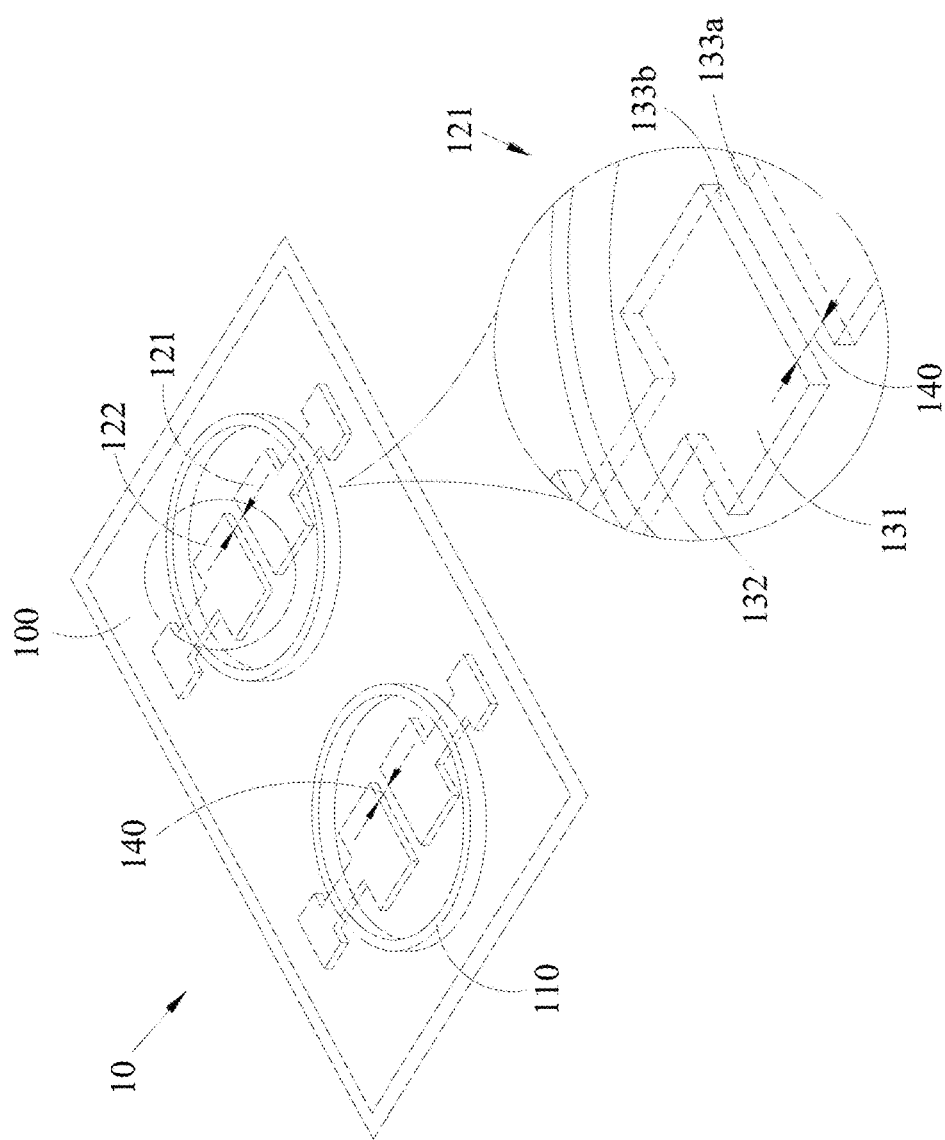
FIG. 1 depicts the top angle view of the apparatus for measuring the conductance parameter of a high protein sample in accordance with one embodiment of the present invention.

As used herein, the articles "a" and "an" refer to one or more than one (i.e., at least one) of the grammatical object of the article. By way of example, "a liquid collection element" means one liquid collection element or more than one liquid collection elements.

The term "subject" can refer to a vertebrate who is dehydrated or to a vertebrate deemed to be in need of rehydration treatment. Subjects include warm-blooded animals, such as mammals, such as a primate, and, more preferably, a human. Non-human primates are subjects as well. The term subject includes domesticated animals, such as cats, dogs, etc., livestock (for example, cattle, horses, pigs, sheep, goats, etc.) and laboratory animals (for example, mouse, rabbit, rat, gerbil, guinea pig, etc.). Thus, veterinary uses and medical formulations are contemplated herein.

All numbers herein may be understood as modified by "about." In one embodiment, the term "about," when referring to a measurable value such as an amount, a temporal duration, and the like, is meant to encompass variations of ±10%, preferably ±5%, more preferably ±1%, and even more preferably ±0.1% from the specified value, as such variations are appropriate to the electric conductance of saliva, unless other specified. As used herein, the term "about," when referring to a range, is meant to encompass variations of ±10% within the difference of the range, preferably ±5%, more preferably ±1%, and even more preferably ±0.1% from the specified value, as such variations are appropriate to the electric conductance of saliva, unless other specified.

Saliva is a potential diagnostic tool for dehydration, as it is rapidly accessible and convenient to collect. Saliva comprises about 99% of water, about 0.2% inorganic substances such as $Na^+$, $K^+$, $Ca^{2+}$, $Mg^{2+}$, $Cl^-$, $HCO_3^-$, $HPO_3^{2-}$ and about 0.7% organic substances such as protein, for examples, IgA, amylase and carbonic anhydrase. The primary secretion from salivary glands is plasma ultrafiltrate but in salivary ducts there is energy-dependent resorption of $Na^+$ and $Cl^-$ resulting in a hypotonic fluid secretion, with a lower ion concentration compare to plasma. The presence of mineralocorticoid receptors in the salivary duct lead to a higher salivary $K^+$ concentration compare to plasma $K^+$ concentration (25 vs. 4 mmol/l) and a lower salivary $Na^+$ concentration compare to plasma $Na^+$ concentration (2 vs. 145 mmol/l). The protein concentration in saliva is about 0.04 to about 8 mg/ml, whereas the protein concentration in the urine is about 0-20 mg/dl or 0 to 0.2 mg/ml (see U.S. National Library of Medicine, MedlinePlus, https://www.nlm.nih.gov/medlineplus/ency/article/003580.htm). The higher saliva protein concentration poses a unique problem for salivary conductance parameters measurement, as the saliva protein adheres to the surface of the electrodes and renders the electrodes less sensitive for electric conductance and/or impedance measurement. One way to prevent protein adhesion to the surface of the electrodes is to coat the electrodes with a layer of anti-fouling coating. However, this approach is not applicable here, as anti-fouling coating on the surfaces of the electrodes renders the electrodes less sensitive for electric conductance and/or impedance measurement.

The present invention addresses this problem, by providing an apparatus for measuring the conductance parameter of a high protein sample, wherein the electrodes of the apparatus are horizontally aligned. The term conductance parameter, as used herein, includes electric conductance (measured in siemens "S") and/or impedance (measured in ohm "Ω"). The conductivity of the high protein sample can be calculated from the measured electric conductance, based on the known formulation or will be apparent, to those skill of art. Other parameters, such as ion concentration (e.g., Na) or osmolality can be measured using the apparatus of the present invention.

A high protein sample, as used herein, includes a sample with a protein concentration between about 0.2 mg/ml to about 10 mg/ml. In one embodiment, the upper limit of the protein concentration of a high protein sample is less than about 15, 14.5, 14, 13.5, 13, 12.5, 12, 11.5, 11, 10.5, 10, 9.5, 9, 8.5, 8 or 7.5. In another embodiment, the lower limit of the protein concentration of a high protein sample is higher than about 1.5, 1, 0.9, 0.8, 0.7, 0.6, 0.5, 0.4 or 0.3 mg/ml. In yet another embodiment, the protein concentration of the high protein sample is any vale or range of values between the upper limit and the lower limit of the protein concentration in 0.01 mg/ml increments (e.g., 0.21 mg/ml, 3.7 mg/ml, 0.4 to 7.1 mg/ml, etc.). In yet another embodiment, the high protein sample is a body fluid is selected from the group consisting of exudates, sweat, saliva, and a combination thereof.

Referring to FIG. 1, which illustrates an apparatus 10 for measuring the conductance parameter of a high protein sample in accordance with one embodiment of the present invention. The apparatus 10 comprises a casing 100, at least one liquid collection element 110, a first electrode 121 and a second electrode 122 disposed in the liquid collection element 110. Each electrode has a top surface 131, a bottom surface 132 and at least one edge 133a and 133b.

The first electrode 121 and the second electrode 122 are substantially horizontally aligned with a gap 140 therebetween. The term horizontally aligned, as used herein, refers to the alignment wherein one of the edge surfaces of the first electrode faces one of the edge surfaces of the second electrode In one embodiment, horizontal aligned refers tothe edge 133a of the first electrode 121 faces the edge 133b of the second electrode 122, as shown in FIG. 1.

Figure 2:
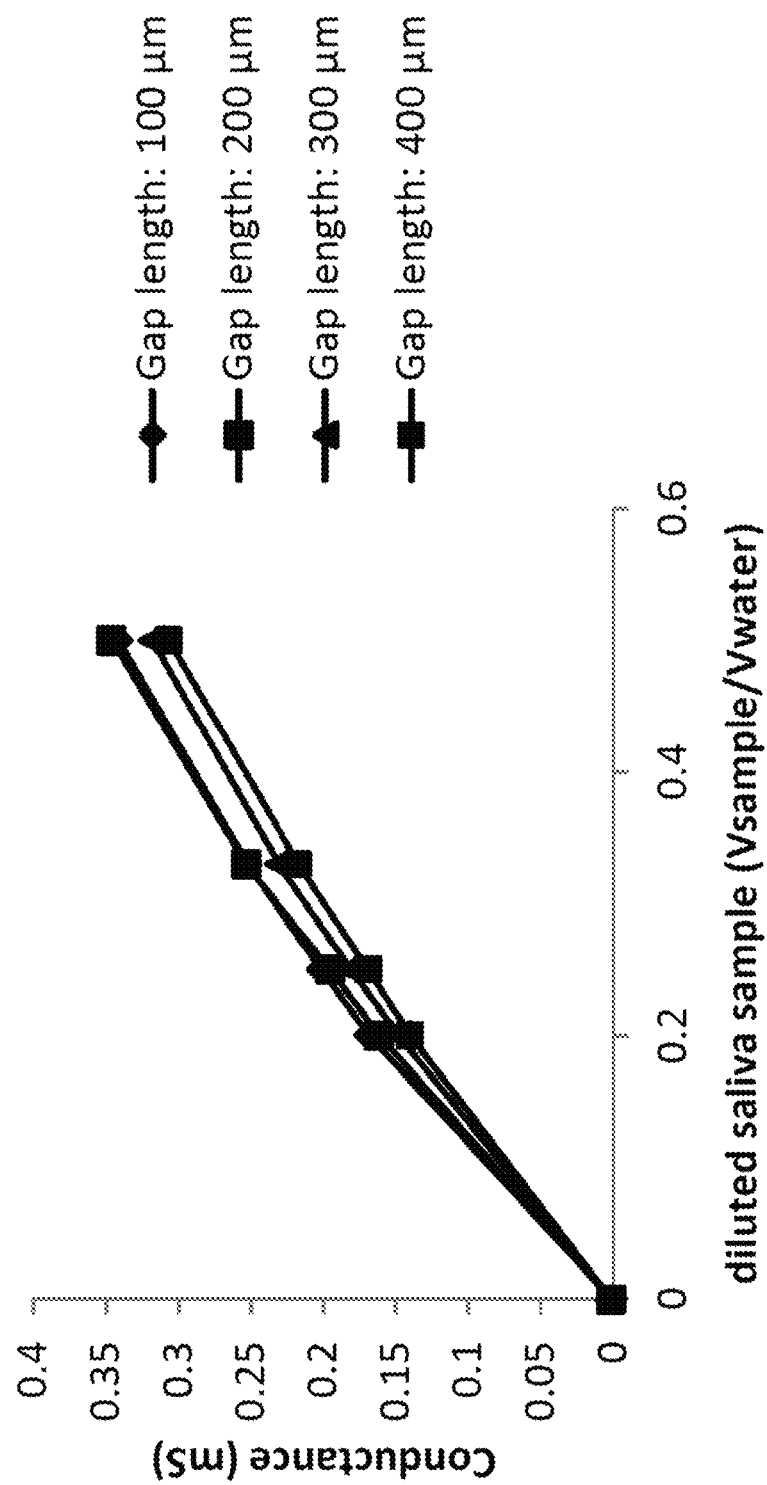
FIG. 2 illustrates the electric conductance of various diluted saliva samples using the apparatus of the present invention with different gap lengths between the electrodes of the apparatus.

Specifically, the gap 140 between the edge of the first electrodes 133a and the edge of the second electrode 133b is about 50 μm to about 500 μm. As show in FIG. 2, the gap lengths of 100 μm to about 400 μm are linearly correlated with different salivary ion concentration and are sensitive to measure the electric conductance of a saliva sample with various dilutions ("0.2" on the X-axis indicates the saliva is 5 times diluted, "0.4" on the X-axis indicates the saliva is 2.5 times diluted). In one exemplary embodiment, the gap 140 is about 50, about 100, about 150, about 200, about 250, about 300, about 350, about 400, about 450, about 500 μm or any vale or range of values therebetween in 1 μm increment (e.g., 59 μm to 377 μm or 100 μm to 400 μm).

The electrodes of the present invention is made of materials known or will be apparent, to those skill of art. In one embodiment, the electrode is made of a material selected from gold, platinum and a combination thereof. In another embodiment, the electrode is substantially free of an anti-fouling coating. Anti-fouling coating, as used herein, include any paint or coating that is applied to slow the adhesion of protein to the surface of the electrode.

Figure 4:
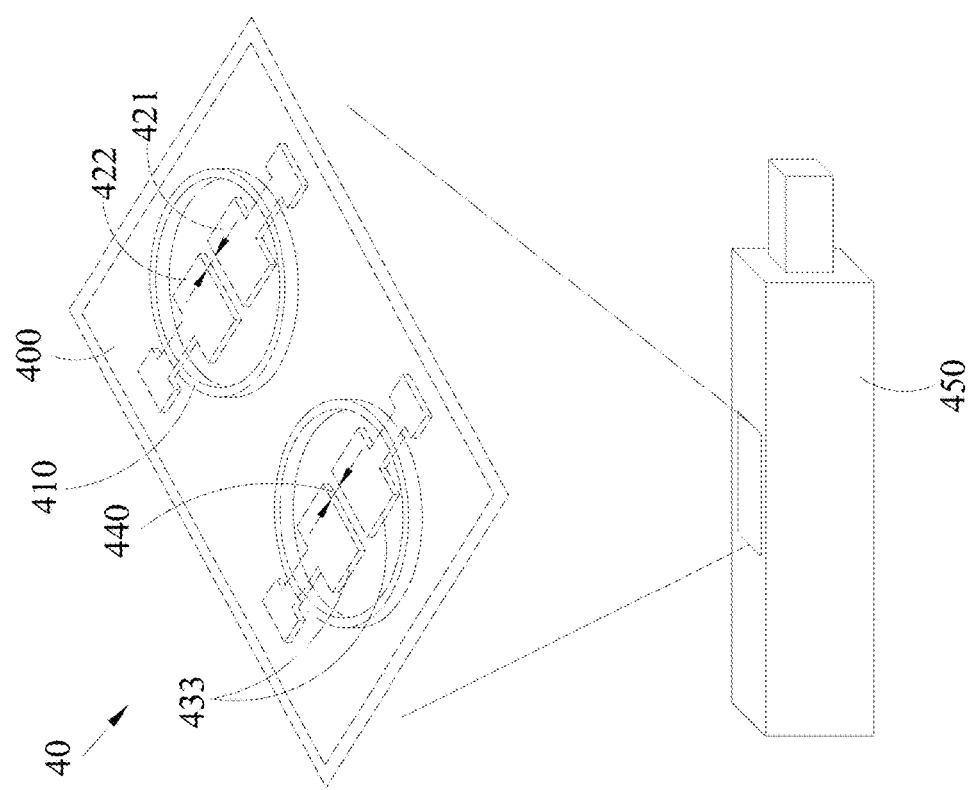
FIG. 4 depicts the top angle view of the apparatus for measuring the conductance parameter of a high protein sample in accordance with another embodiment of the present invention.

In one embodiment, the apparatus 10 further comprises a chip to measure various parameters of the sample, such as ion concentration, electric conductance or impedance. In another embodiment, the apparatus further comprises a display to show the results of the measurement, and/or if the subject is dehydrated. In another embodiment, as shown in FIG. 4, the apparatus 40 is connected to a device 450 comprising a chip for reading and/or a display for showing the results of the measurements in tested sample. Non limiting examples of the device 450 include USB drive, a portable electronic detector, a smartphone, a smartwatch, a pad or a laptop. In one embodiment, the results of the tested sample are stored in the device 450 and can be transferred to another device for further analysis. In an exemplary embodiment, the device 450 is an LCR meter (a meter to measure inductance (L), capacitance (C) and resistance (R)).

The apparatus of the present invention is portable and compact. Hence, only a small amount of the tested sample is required, as long as the saliva can cover the edges of the electrodes in the liquid collection element. In some embodiments, about 20 μl to about 1.5 ml of the tested sample is required, or any value or range of values therebetween in 10 μl increment (e.g., 50 μl, 0.1-0.15 ml etc.).

Also provided are methods for detecting dehydration of a subject, comprising the steps of measuring the conductance parameter of the saliva of the subject, wherein the saliva conductance parameter is electric conductance or impedance, and a higher saliva electric conductance in the subject, relative to the saliva electric conductance of a non-dehydrated subject, is indicative the subject is dehydrated or a lower saliva impedance in the subject, relative to the saliva impedance of a non-dehydrated subject, is indicative the subject is dehydrated.

In one embodiment, the saliva conductance parameters are measured by the apparatus described herein. In another embodiment, the saliva sample is diluted with a fluid suitable for diluting the saliva ("the dilution fluid"), such as deionic water, before measuring the conductance parameter. Such dilution before the measuring the conductance parameter reduces the froth in the saliva and increase the sensitivity of the measurement. In an exemplary embodiment, the ratio of the saliva to the dilution fluid ("the dilution ratio) is 1:1, 1:1.5, 1:2, 1:2.5, 1:3, 1:3.5, 1:4, 1:4.5, 1:5, 1:5.5, 1:6, 1:6.5, 1:7, 1:7.5, 1:8, 1: 8.5, 1:9, 1:9.5 or 1:10 (v:v).

In one embodiment, the lower limit of the saliva electric conductance indicative of dehydration is about 0.1, 0.15, 0.2, 0.25, 0.3, 0.35, 0.4, 0.45, 0.5, 0.55, or 0.6 mS, if the dilution ratio is 1:4 (v:v). In another embodiment, the upper limit of the saliva electric conductance indicative of dehydration is about 2, 1.9, 1.8, 1.7, 1.6, 1.5, 1.4, 1.3, 1.2, 1.1, 1, 0.95, 0.9, 0.85, 0.8, 0.75, 0.7, 0.65, 0.6 mS, if the dilution ratio is 1:4 (v:v). In yet another embodiment, the saliva electric conductance indicative of dehydration is a value or range of values between the upper limit (2 mS) and the lower limit (0.25 mS) of the saliva electric conductance in 0.01 mS increment (e.g., 0.4 mS, 0.25-0.55 mS, 0.3-0.5 mS,0.35-0.45 mS, 0.25-0.45, 0.28-0.78 mS, 0.28 to 1 mS, 0.23 mS to 0.35 mS), if the dilution ratio is 1:4 (v:v).

The saliva electric conductance indicative of dehydration can be calculated for other saliva dilution ratios. For example, if the saliva dilution ratio is 1:1 (v:v), the saliva electric conductance indicative of dehydration is calculated as follows: (saliva electric conductance indicative of dehydration when the saliva dilution ratio of 1:4 (v:v))*5/2; if the dilution ratio is 1:2 (v:v), the saliva electric conductance indicative of dehydration is calculated as follows: (saliva electric conductance indicative of dehydration when the saliva dilution ratio of 1:4 (v:v))*5/3.

In some embodiments, the saliva conductance parameter is impedance, and conductance can be calculated from impedance by the following formula:

$$Y=1/Z, Y=G+jB,$$

wherein Y is the admittance, Z is the impedance, G is the conductance, jB is the imaginary part of admittance. In one embodiment, the saliva impedance indicative of dehydration is about 500Ω to about less than 3500Ω if the dilution ratio is 1:4 (v:v), or any value or any range of values therebetween in 10Ω increment (e.g., 600Ω, 700Ω, 800Ω, 900Ω, 1000Ω, 1100Ω, 1200Ω, 1300Ω, 1400Ω, 1500Ω, 1600Ω, 1700Ω, 1800Ω, 1900Ω, 2000Ω, 2100Ω, 2200Ω, 2300Ω, 2400Ω, 2500Ω, 2600Ω, 2700Ω, 2800Ω, 2900Ω, 3000Ω, 3100Ω, 3200Ω, 3300Ω, 3400Ω, or about 1000Ω-about 3200Ω etc.)

In some embodiments, the saliva is stimulated and collected. In other embodiments, the saliva is unstimulated and collected. Saliva secretion can be stimulated by administering at least one of the following agent to the subject: olfactory salivary stimulating agent, gustatory salivary stimulating agent, or mechanical salivary stimulating agent.

Embodiments of the present invention are illustrated by the following examples, which are not to be construed in any way as imposing limitations upon the scope thereof. During the studies described in the following examples, conventional procedures were followed, unless otherwise stated. Some of the procedures are described below for illustrative purpose.

EXAMPLE 1

Evaluation of the Relationship Between Saliva Electric Conductance and Dehydration 15 saliva samples were collected from subjects with dehydration (based on blood urea nitrogen/creatinine ratio≥15) and 5 normal saliva samples were collected from subjects without dehydration. The saliva was diluted 5 times with deionic water (i.e., the dilution ratio is 1:4 (v:v)).

The diluted saliva was placed between the electrodes depicted in FIG. 1 and saliva conductance was measured using Agilent Semiconductor device analyzer B1500A (Keysight Technologies, USA).

Figure 3:
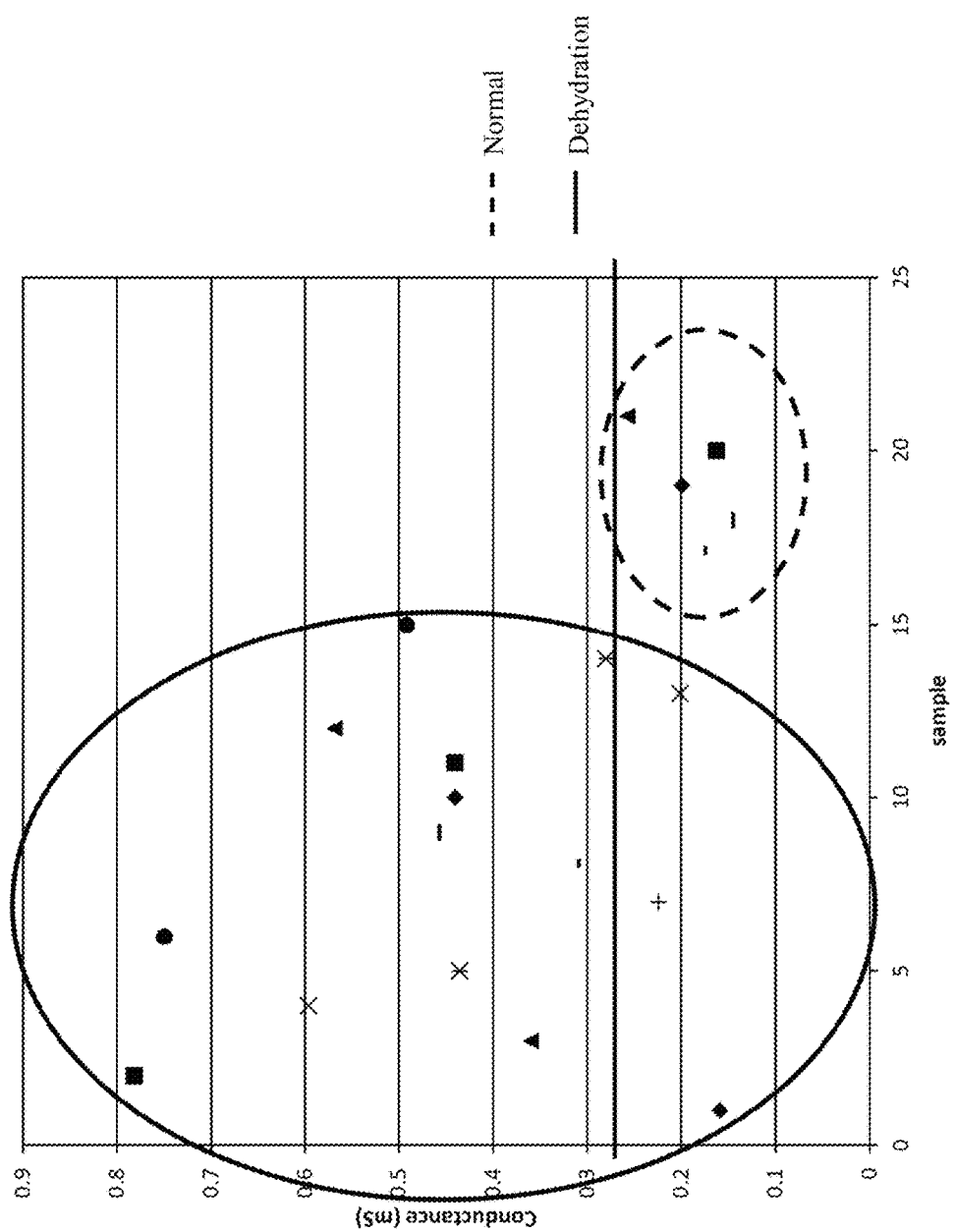
FIG. 3 shows the saliva electric conductance of normal and dehydrated samples, measured with the apparatus depicted in FIG. 1.

Results: FIG. 3 shows the saliva electric conductance of the dehydrated subjects ranged from 0.16 mS to about 0.78 mS (95% confidence interval is 0.10 mS-0.28 mS). The saliva electric conductance of the normal (non-dehydrated) subjects was below 0.28 mS. The results show the saliva electric conductance higher than 0.28 mS is consistent with the diagnosis of dehydration.

A second study of 15 dehydrated saliva samples (based on blood urea nitrogen/creatinine ratio≥15, measured by Beckman DXC 880i) and 15 normal saliva samples (based on blood urea nitrogen/creatinine ratio<15) was conducted. The saliva was stored at −80° C. and diluted 5 times with deionic water before the analysis (the saliva dilution ratio is 1:4). 50 μL of diluted saliva was placed between the electrodes depicted in FIG. 1 and saliva impedance and saliva conductance were measured using LCR meter HIOKI IM3533 (Hioki E.E. Corporation, Japan).

Figure 7A:
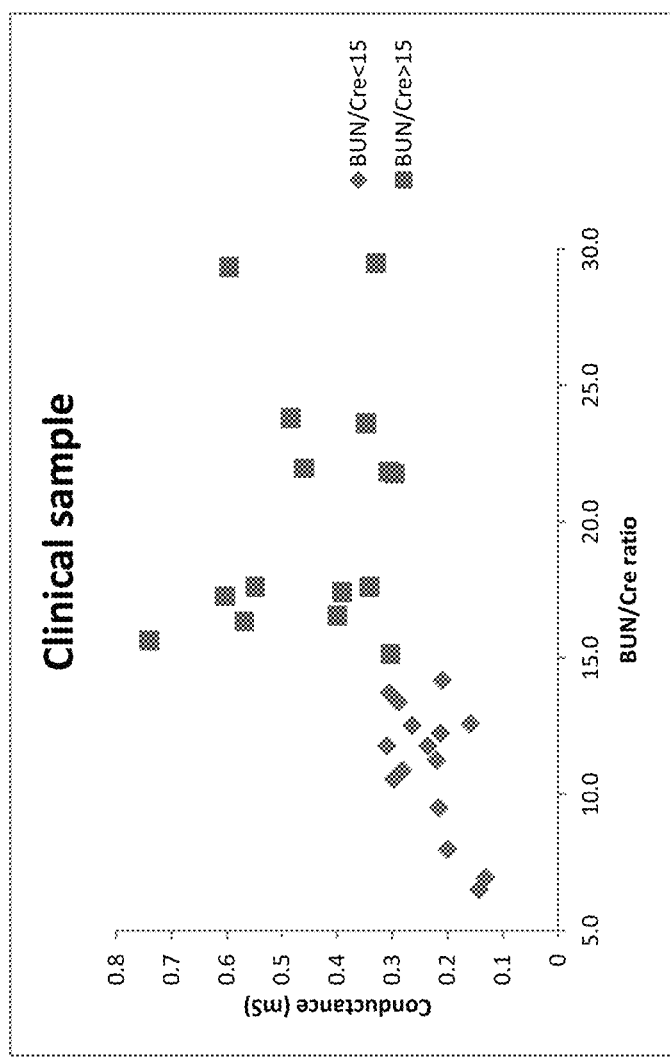
FIG. 7A and FIG. 7B show the saliva electric conductance (FIG. 7A) and saliva impedance (FIG. 7B) of normal and dehydrated samples of a second study, measured with the apparatus depicted in FIG. 1.
Figure 7B:
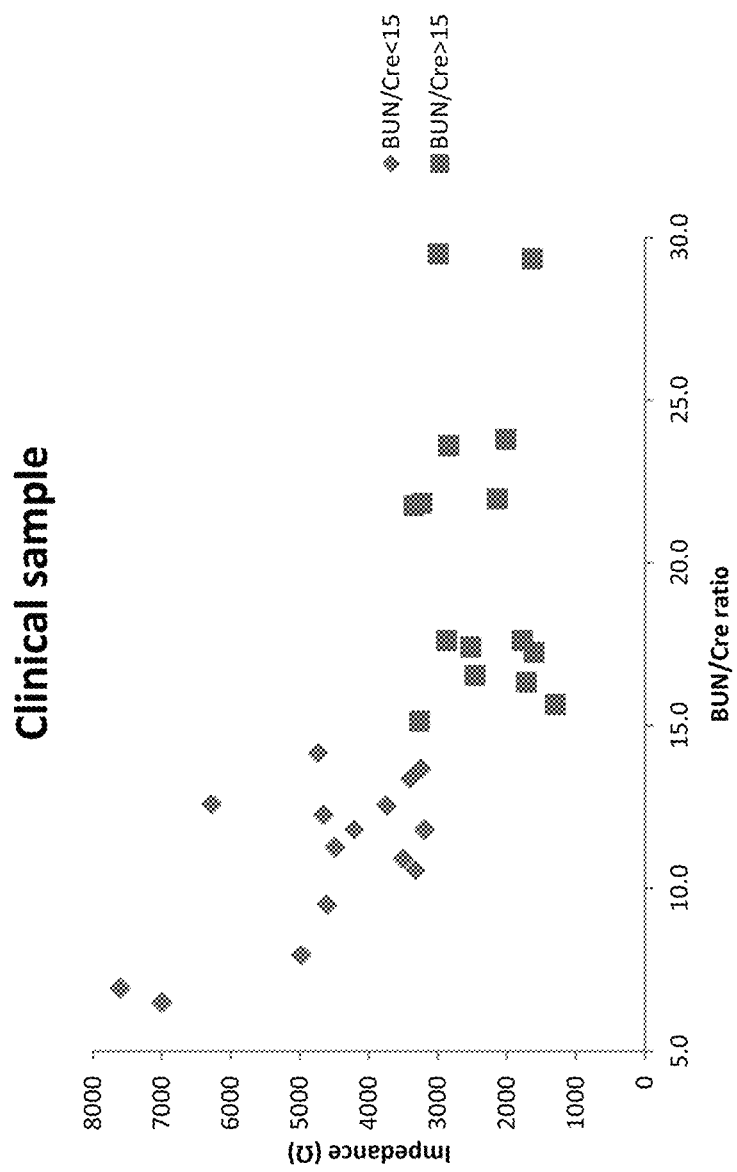

Results: FIG. 7A shows the saliva conductance of the dehydrated subjects and the normal subjects. The mean saliva conductance of the dehydrated subjects is 0.4 mS whereas the mean saliva conductance of the normal subjects is 0.23 mS and the difference is statistically significant (P<0.05). The lower limit of saliva conductance for dehydration is about 0.34 mS. FIG. 7B shows the saliva impedance of the dehydrated subjects and the normal subjects. The mean saliva impedance of the dehydrated subjects is 2377.7Ω whereas the mean saliva impedance of the normal subjects is 4593.3Ω and the difference is statistically significant (P<0.05).

EXAMPLE 2

In Vitro Evaluation of Vertical Aligned Electrodes and Horizontally Aligned Electrodes on Conductance Parameter Tested Samples: The amount of NaCl in all the samples was fixed (5 mM NaCl) but the protein concentration varied from 0 mg/ml, 0.043 mg/ml, 1.0 mg/ml, 3.5 mg/ml, 7.0 mg/ml, 10 mg/ml, 15 mg/ml to 20 mg/ml.

Figure 6B:
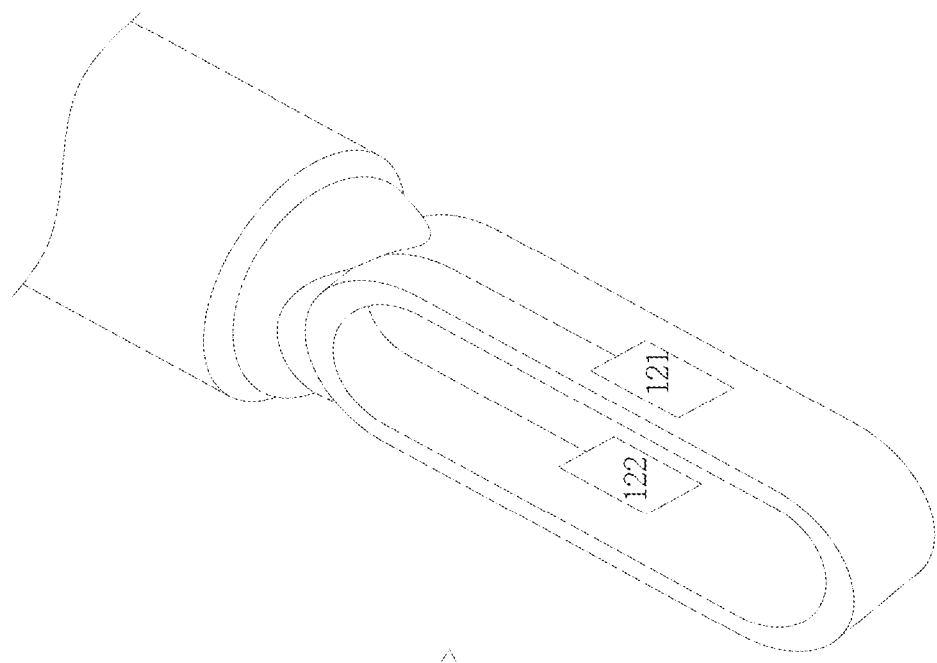

Procedure: briefly, 50 μl of the tested sample was placed into the liquid collection element and the electric conductance of the tested sample was measured using (a) a commercial probe (Catalogue type: DJS-1, commercially available from Ruosull Technology, China), as illustrated in FIG. 6B wherein the electrodes 121 and 122 are vertically aligned, and (b) the apparatus of FIG. 6A, wherein the electrodes 121 and 122 are horizontally aligned. Given the amount of NaCl was fixed in all of the test samples, there should be minimal variation in electric conductance.

Figure 5:
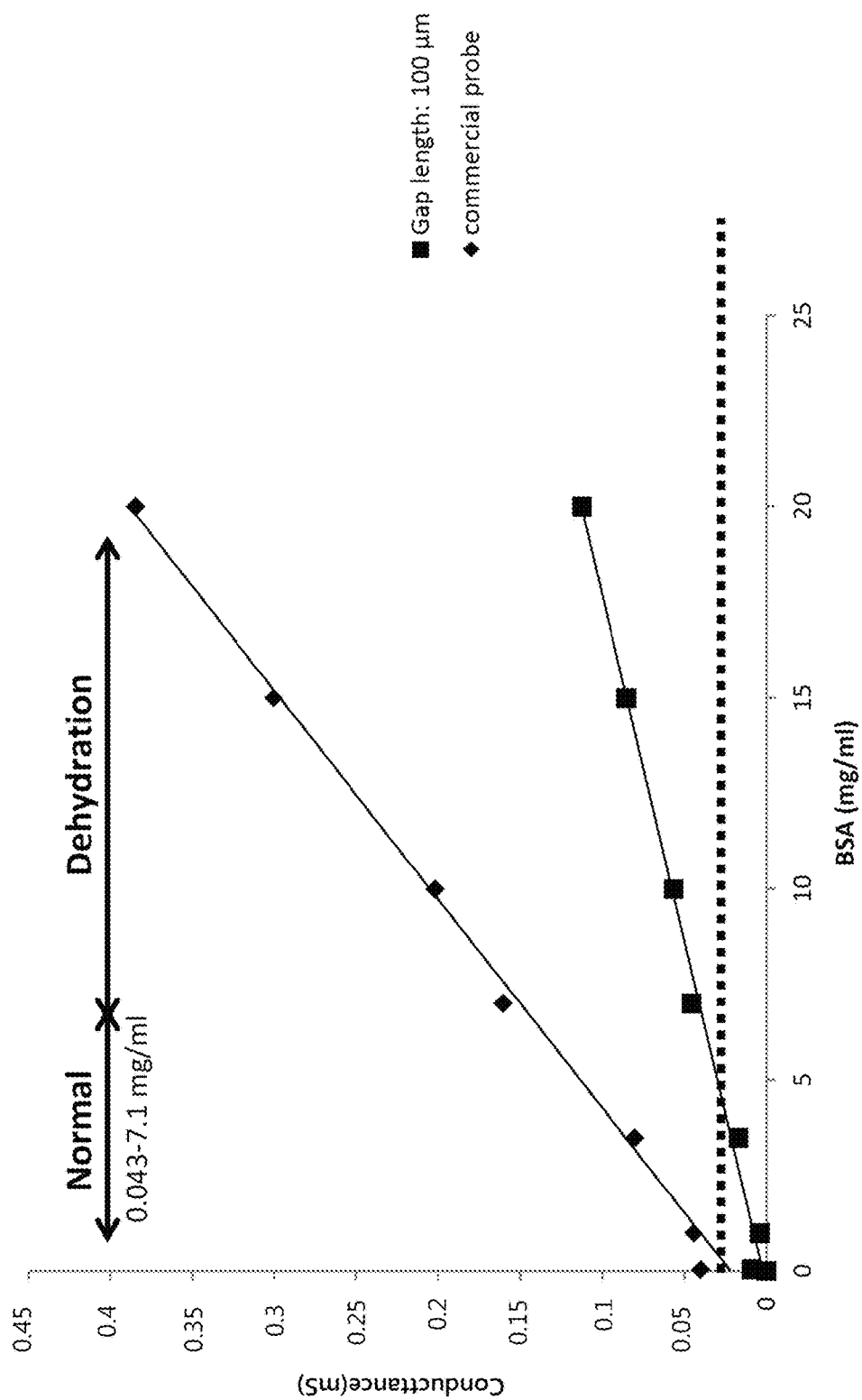
FIG. 5 is a graph illustrate the electric conductance of samples with a fixed amount of NaCl but various protein concentrations, measured with a commercially available device (illustrated in FIG. 6B) and measured with apparatus of the present invention (illustrated in FIG. 6A).
Figure 6A:
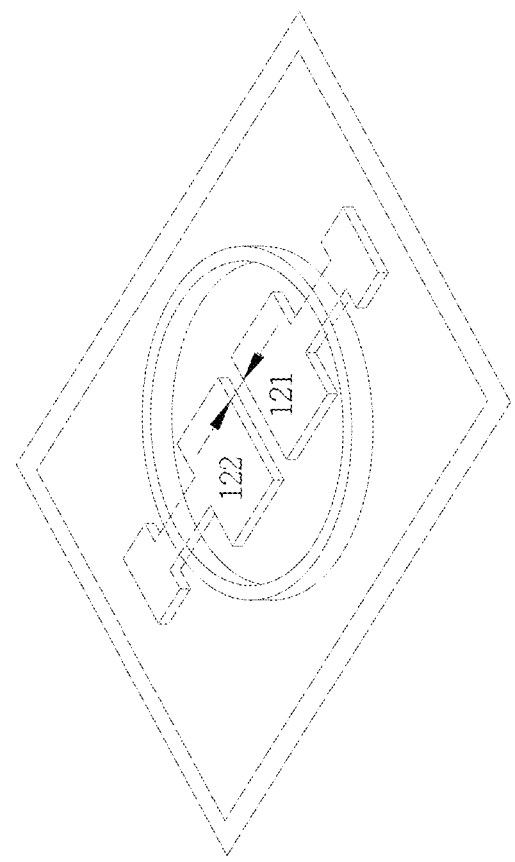

Results: FIG. 5 illustrates the electric conductance of the tested samples. Given the amount of NaCl was fixed in all of the samples, the conductance of all of the samples, despite different protein concentration, should be the same (as the dotted horizontal line at the bottom of FIG. 5). There is a huge variation in the electric conductance measured by the commercial probe of FIG. 6B but less variation in the electric conductance measured by the apparatus of FIG. 6A, compared to the dotted horizontal line. The results indicate there is less interference or adhesion of protein on the edge of the horizontally aligned electrodes. Hence, the apparatus of the present invention provides a more accurate measurement of the electric conductance of a high protein sample.

What is claimed is:

1. A method for detecting dehydration in a subject, comprising:
    measuring saliva electric conductance or saliva electric impedance of the subject, and
    identifying the subject as having dehydration if the subject has a higher saliva electric conductance, relative to the saliva electric conductance of a non-dehydrated subject or if the subject has a lower saliva electric impedance in the subject, relative to the saliva electric impedance of a non-dehydrated subject,
    wherein the saliva electric conductance or saliva electric impedance is measured by an apparatus comprising:
        at least one liquid collection element; and
        a first electrode and a second electrode in the liquid collection element, each electrode having a top surface, a bottom surface and at least one edge,
    wherein the first electrode and the second electrode are substantially horizontally aligned with a gap between the edge of the first electrode and the edge of the second electrode, and said edge of the first electrode is facing said edge of the second electrode.

2. The method of claim 1, wherein the electrode is substantially free of anti-fouling coating.

3. The method of claim 1, wherein the volume of the saliva for measuring salivary conductance is about 20 μl to about 1.5 ml.

4. The method of claim 1, wherein the saliva is diluted with a dilution fluid before measuring the electric conductance or saliva impedance.

5. The method of claim 1, wherein the gap between the edge of the first electrode and the edge of the second electrode is about 50 μm to about 500 μm.

6. The method of claim 1, wherein the gap between the edge of the first electrode and the edge of the second electrode is about 100 μm to about 400 μm.

7. The method of claim 1, wherein the gap between the edge of the first electrode and the edge of the second electrode is about 100 μm.

* * * * *